United States Patent
Ouchi

(10) Patent No.: US 7,630,588 B2
(45) Date of Patent: Dec. 8, 2009

(54) HIGH FREQUENCY ELECTRICAL SIGNAL CONTROL DEVICE AND SENSING SYSTEM

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 738 days.

(21) Appl. No.: 10/541,240

(22) PCT Filed: Mar. 26, 2004

(86) PCT No.: PCT/JP2004/004348

§ 371 (c)(1),
(2), (4) Date: Jul. 1, 2005

(87) PCT Pub. No.: WO2005/001505

PCT Pub. Date: Jan. 6, 2005

(65) Prior Publication Data

US 2006/0085160 A1 Apr. 20, 2006

(30) Foreign Application Priority Data

Jun. 25, 2003 (JP) .............................. 2003-181663
Jun. 25, 2003 (JP) .............................. 2003-181664

(51) Int. Cl.
*G02F 1/295* (2006.01)
*G02F 1/035* (2006.01)
*G02B 6/00* (2006.01)
*G02B 6/26* (2006.01)
*G02B 6/42* (2006.01)

(52) U.S. Cl. ............... 385/8; 385/1; 385/2; 385/4; 385/12; 385/40; 385/41; 385/45; 359/331; 359/332; 250/358.1; 250/393; 250/216; 250/227.11; 250/227.12

(58) Field of Classification Search ............... 385/4, 385/8, 12, 40, 41, 45; 359/331, 332; 250/358.1, 250/393, 227.12
See application file for complete search history.

(56) References Cited

U.S. PATENT DOCUMENTS

| | | | |
|---|---|---|---|
| 5,586,131 A | 12/1996 | Ono et al. | 372/19 |
| 5,659,560 A | 8/1997 | Ouchi et al. | 372/27 |
| 5,699,373 A | 12/1997 | Uchida et al. | 372/27 |

(Continued)

FOREIGN PATENT DOCUMENTS

EP 0 354 308 2/1990

(Continued)

OTHER PUBLICATIONS

European Search Report dated Feb. 25, 2008 in European Application No. 0715006.

(Continued)

*Primary Examiner*—Ryan Lepisto
(74) *Attorney, Agent, or Firm*—Fitzpatrick, Cella, Harper & Scinto

(57) ABSTRACT

A high frequency electrical signal control device comprises a transmitter for generating a high frequency electrical signal, a receiver, a transmission line for propagating the electrical signal, and a structure for radiating the electrical signal propagated through the transmission line to the space or receiving a signal from the space. The degree of coupling of the electrical signal between the space and the transmission line provided by the structure can be variably controlled.

12 Claims, 14 Drawing Sheets

U.S. PATENT DOCUMENTS

| | | | |
|---|---|---|---|
| 5,764,670 A | 6/1998 | Ouchi | 372/45 |
| 5,789,750 A | 8/1998 | Nuss | 250/338.1 |
| 5,850,612 A | 12/1998 | Kulberg et al. | 455/550 |
| 6,268,833 B1 | 7/2001 | Tanizaki et al. | 343/766 |
| 6,388,799 B1 | 5/2002 | Arnone et al. | 359/326 |
| 6,566,617 B1 | 5/2003 | Suzuki et al. | 200/181 |
| 2001/0029436 A1 | 10/2001 | Fukasawa | 702/117 |
| 2001/0049266 A1 | 12/2001 | Hayata et al. | 455/81 |
| 2006/0085159 A1 | 4/2006 | Itsuji et al. | 702/150 |
| 2006/0188398 A1 | 8/2006 | Yano et al. | 422/82.01 |
| 2006/0197021 A1 | 9/2006 | Ouchi | 250/343 |
| 2006/0214176 A1 | 9/2006 | Ouchi et al. | 257/98 |
| 2006/0227340 A1 | 10/2006 | Shioda et al. | 356/614 |
| 2006/0244629 A1 | 11/2006 | Miyazaki et al. | 340/855.7 |
| 2007/0030115 A1 | 2/2007 | Itsuji et al. | 340/5.8 |

FOREIGN PATENT DOCUMENTS

| | | |
|---|---|---|
| EP | 0 606 776 | 7/1994 |
| EP | 0828143 | 3/1998 |
| EP | 0 852 409 | 7/1998 |
| EP | 0852409 | 7/1998 |
| GB | 2371618 | 7/2002 |
| JP | 10-104171 | 4/1998 |
| JP | 10-200331 | 7/1998 |
| JP | 11-513548 | 11/1999 |
| JP | 2000-22424 | 1/2000 |
| JP | 2000-162656 | 6/2000 |
| JP | 2000-188049 | 7/2000 |
| JP | 2000-269724 | 9/2000 |
| JP | 2001-50908 | 2/2001 |
| JP | 2002-098634 | 4/2002 |
| JP | 2003-195380 | 7/2003 |
| WO | 97/13290 | 4/1997 |
| WO | 00/38208 | 6/2000 |

OTHER PUBLICATIONS

European Official Action dated Feb. 28, 2008 in European Application No. 04723792.

Nuss M C: "Chemistry Is Right for T-ray Imaging Laser, Microwave, and Signal Processing Technologies a Perfect Blend for Applications in Packaging, Security, and Quality Control" IEEE Circuits and Devices Magazine, IEEE Inc. New York, US, vol. 12, No. 2, Mar. 1, 1996, pp. 25-30, XP000589127 ISSN: 8755-3996.

U.S. Appl. No. 10/587,261 (Sekiguchi, et al.), pending filed Jul. 26, 2006.

Masahiko Tani, et al., "Generation of coherent terahertz radiation by photomixing of dual-mode lasers", Optical and Quantum Electronics, May 2000, vol. 32, No. 4/5, pp. 503-520.

Masaharu Hyodo, et al., "Optical Generation of Milllmeter-Wave Signals Up to 330 GHz by Means of Cascadingly Phase Locking Three Semiconductor lasers", IEEE Photonics Technology Letters, Mar. 2003, vol. 15, No. 3, pp. 458-460.

HIGH FREQUENCY ELECTRICAL SIGNAL CONTROL DEVICE AND SENSING SYSTEM

TECHNICAL FIELD

The present invention relates to a high frequency electrical signal control device for generating a high frequency electrical signal mainly ranging from a millimeter wave to a terahertz wave, and a sensing system using the same.

BACKGROUND ART

In recent years, there has been developed a nondestructive sensing technique using an electromagnetic wave (its frequency is in a range of 30 GHz to 30 THz) ranging from a millimeter wave to a terahertz wave. As for a technique using the electromagnetic wave having this frequency band, there are developed a technique for carrying out imaging using a safe penetrative inspection system instead of an X-ray system, and a technique for obtaining an absorption spectrum or a complex permittivity of the inside of a substance to evaluate a bonding state of atoms, or concentration or mobility of carriers. In addition, as for a technique using a millimeter wave, there is developed a position sensing technique for a collision safety radar having a frequency in 70 GHz band.

For example, as for a two-dimensional imaging system, there is a proposal example in which a system is configured with a millimeter wave generator, an antenna for radiating the millimeter wave, a reception element, a propagation path for the millimeter wave, and the like being used as discrete components (refer to Japanese Patent Application Laid-Open No. 2001-050908). This system is shown in FIG. 8. This system is designed such tat a millimeter wave 116 is radiated from a sinusoidal millimeter wave generator 102 to the space through an antenna 112, and the millimeter wave 116 having an intensity distribution is received by an electro-optic crystal 110 having light reflecting film 111 and directed by reflectors 109 through wave plates 107 and 108 to be read with a laser beam from a laser 104. The system also includes sinusoidal wave generators 101 and 103. At this time, a phase difference in the millimeter wave caused on the basis of a difference in permittivity of a specimen object 113 is detected by utilizing a synchronism wave detection technique and polarization beam splitter 106, photodiode 105, computer 114 and lock-in amplifier 115 to obtain penetrative imaging excellent in an S/N ratio.

On the other hand, as for the position sensing technique, an on-vehicle millimeter wave radar is in a progress of being developed for the purpose of measuring a distance between a forward vehicle and a backward vehicle. As for a proposal example thereof, there is a transmitter-receiver which is constructed in the form of a module as shown in FIG. 9 using a non-radiative dielectric Line (NRD) (refer to Japanese Patent Application Laid-Open No. 2000-022424). In this example, a millimeter wave outputted from a millimeter wave oscillator provided in an unmovable portion 232 is propagated through an NRD 221 to reach a primary radiator 213 provided in a movable portion 231 through a circulator 219 and couplers 212 and 211 to be received by a horn antenna (not shown) provided above the primary radiator 213. In this connection, the movable portion 231 is moved to be adapted to carry out the scanning for a radiation directional angle of the millimeter wave. After received by the same horn antenna, the millimeter wave is mixed with a millimeter wave which is obtained by a coupler 221 through the branch of a part of the millimeter wave from the oscillator, in a coupler 223 through the circulator 219. The module also includes transmission line 222 having termination devices 220. In such a manner, the millimeter wave concerned is received. From the foregoing, the millimeter module capable of making a detection direction variable is constructed.

DISCLOSURE OF THE INVENTION

Now, in recent years, such a ubiquitous module as to be miniature and portable has become necessary in such penetrative imaging and position sensing because an application as a device for simply inspecting various materials and living body information, and an application as a pointing device in an information apparatus (for example, this module is used as a device for sensing a spatial position of a pen type input unit) are expected.

In this case, the system constructed using the discrete components as in the conventional example of FIG. 8 is large in scale. In addition, in a method in which when two-dimensional imaging is carried out, a beam is expanded to collectively carry out the measurement, a high speed operation is obtained. However, since it is necessary to increase a millimeter wave output, this method has a problem in power consumption. Also, in case of the transmitter-receiver of FIG. 9 which is constructed in the form of the module so as to allow the beam scanning to be carried out using the NRD, this problem is solved. However, it is required that accuracy in manufacture of the NRD, and accuracy in installation position with the couplers, the circulator and the like are high. As a result, there is a problem in that the transmitter-receiver becomes high in cost, and hence is not suitable for mass production. In addition, since a motor must be used in order to carry out the beam scanning, this becomes an obstacle to power saving and miniaturization.

In the light of the foregoing, it is an object of the present invention to provide a high frequency electrical signal control device which serves to carry out sensing or the like using an electromagnetic wave mainly ranging from a millimeter wave to a terahertz wave, and which can be readily constructed in the form of a miniature and portable integrated module low in power consumption, and a sensing system using the same.

A high frequency electrical signal control device according to the present invention includes a generator for generating a high frequency electrical signal which serves as an element for converting a laser beam into an electromagnetic wave having a frequency lower than that of the laser beam, wherein a laser device such as a semiconductor laser or a solid-state laser for generating a laser beam, an optical waveguide for propagating the laser beam to guide the laser beam to a generator, the generator, and a transmission line for propagating the signal are provided (integrated) on the same substrate. According to the high frequency electrical signal control device having this construction, it is possible to readily obtain a construction such as a module in which the laser device such as a miniature semiconductor laser, and the optical waveguide for guiding the laser beam to the generator are integrated together with the generator and the transmission line for propagating the signal from the generator on the same substrate. Moreover, it is also possible to obtain a form in which a detector and a transmission line for propagating the signal to the detector are further integrated on the same substrate. In addition, it is possible to obtain a form in which a dielectric member constituting the optical waveguide and a dielectric insulating layer constituting the transmission line are formed of the same member. In this example, since the optical waveguide and the transmission line for propagating a signal are formed of the same member, it is possible to readily provide a miniature module which is easy in manufacture and is relatively low in cost. Moreover, if a detector and an antenna are provided, transmission/reflection measurement can be simply carried out anywhere for all specimens such as semiconductors, organic substances, and living bodies, whereby permittivity, carrier concentration distribution, and the like can be examined in a contact or non-contact manner, and inspection, authentication, security check, and the like of DNA, protein, and the like can be carried out.

A high frequency electrical signal control device according to the present invention includes a transmitter for generating a high frequency electrical signal, a receiver, a transmission line for propagating the electrical signal, and a structure for radiating the electrical signal propagated through the transmission line to the space or receiving a signal from the space, wherein a degree of coupling of the electrical signal between the space and the transmission line provided by the structure can be variably controlled. In addition, a high frequency electrical signal control device according to the present invention includes a transmitter for generating a high frequency electrical signal, a receiver, a transmission line for propagating the electrical signal, and a structure for radiating the electrical signal propagated through the transmission line to the space or receiving a signal from the space, wherein the structure has a movable portion, and directivity of an electromagnetic wave radiated to the space can be controlled in deflection. According to the construction of the controller of the present invention, a microwave integrated circuit (MIC) technique applicable to formation of the transmission line or the like, and a microelectromechanical systems (MEMS) technique applicable to formation of means for variably controlling the degree of coupling of the electrical signal, the movable portion of the structure, and the like are extended up to a region of a millimeter wave to a terahertz wave to be merged for application to thereby allow the controller to be miniaturized.

The high frequency electrical signal control device as will be described below is possible on the basis of the above-mentioned basic construction.

There may be adopted a construction in which an antenna is provided as the above-mentioned structure so that intensity or directivity of an electromagnetic wave radiated or received through the antenna can be made variable. In addition, there may be adopted a construction in which the above-mentioned transmission line is a microstrip line or a co-planar (co-planar strip) line constituted by a plane circuit, and the above-mentioned structure is formed on the plane circuit. To describe a typical example, a microstrip line, a co-planar line, and the like are formed on a substrate as a plane circuit in which a transmission line for propagating a high frequency signal from the transmitter to the receiver can be formed with high accuracy by utilizing the photolithography technique or the like, and a thin film antenna for radiating/receiving an electromagnetic wave to/from the space, and the like are integrated on the same plane circuit.

In addition, there may be adopted a construction in which a movable portion for turning ON/OFF electrical contact is provided, the movable portion being formed on the plane circuit, so that a degree of coupling of the signal between the structure and the space can be variably controlled by the movable portion. That is, a contact switch and the like which are formed in micro size to be integrated on the same plane circuit are used as means for controlling a ratio of coupling to the antenna. Supply of an electric power to the antenna is carried out in accordance with ON/OFF control by this switch.

In addition, the above-mentioned transmission line is a waveguide as a three-dimensional structure having a rectangular or circular cavity, and the above-mentioned antenna is a horn antenna having a similar cavity. Then, the controller can be constructed such that it is possible to carry out at least one of an operation for changing a positional relationship between an input portion of the horn antenna and the waveguide to change the magnitude of the degree of coupling, and an operation for changing a direction of an output unit of the horn antenna to carry out scanning for the directivity of an electromagnetic wave radiated to the space. That is, the structure itself having the antenna formed therein is moved by utilizing the MEMS technique, whereby intensity control and directivity control for radiation or reception of the electromagnetic wave can also be carried out. This is realized by moving a structure adapted to be vibrated and rotated or by sliding a horn antenna in accordance with an electrostatic method, an electromagnetic method, or the like for example.

In addition, the controller may be constructed such that a photonic crystal or a lens is integrated on a surface of the above-mentioned antenna to emit an electromagnetic wave having high directivity through a narrow-emission angle.

Also, there may be adopted a construction in which a circulator is integrated in the transmission line in order that an electrical signal may be caused to flow in one direction among the transmitter, the receiver, and the structure connected to the transmission line. Also, there may be adopted a construction in which the transmitter and the receiver are integrated on the same substrate.

Moreover, there may be adopted a construction in which the transmitter for generating the high frequency electrical signal serves to apply a pulse laser beam to a gap defined between two conductors which are provided on a surface of a photoconductive film and across which a voltage is applied and the receiver serves to obtain an electrical signal from a current caused to flow between the two conductors in the same construction, while the reception can be carried out only at a timing when a part of the same pulse laser beam is applied to the gap between the two conductors of the receiver and means for allowing control of an amount of beam delay is provided in the middle of an optical path through which the pulse laser beam is guided to the receiver. In such a manner, as for means for transmitting/receiving the high frequency signal, in addition to a method including using a semiconductor electronic device such as a hetero-bipolar transistor (HBT), or a Schottky barrier diode (SBD), there is a method in which a short pulse laser beam is applied to a photoconductive switching device to generate and detect a short pulse electrical signal.

In the foregoing, a frequency ranging from a millimeter wave band to a terahertz wave band (30 GHz to 30 THz) is typically used as a frequency of the high frequency electrical signal.

Moreover, a feature of a high frequency sensing system according to the present invention is that propagation of an electromagnetic wave through the space is controlled using the above-mentioned high frequency electrical signal control device to wirelessly inspect constituent elements, a permittivity distribution state, positional information, and the like of a surface or the inside of an object. As a result, it is possible to realize the sensing system making the most of the feature of the above-mentioned high frequency electrical signal control device.

BEST MODE FOR CARRYING OUT THE INVENTION

Specific modes of the present invention will hereinafter be concretely described by giving embodiments with reference to the accompanying drawings. It should be noted that materials, structures, devices and the like are not intended to be limited to those which will be given herein.

First Embodiment

Figure 1A:
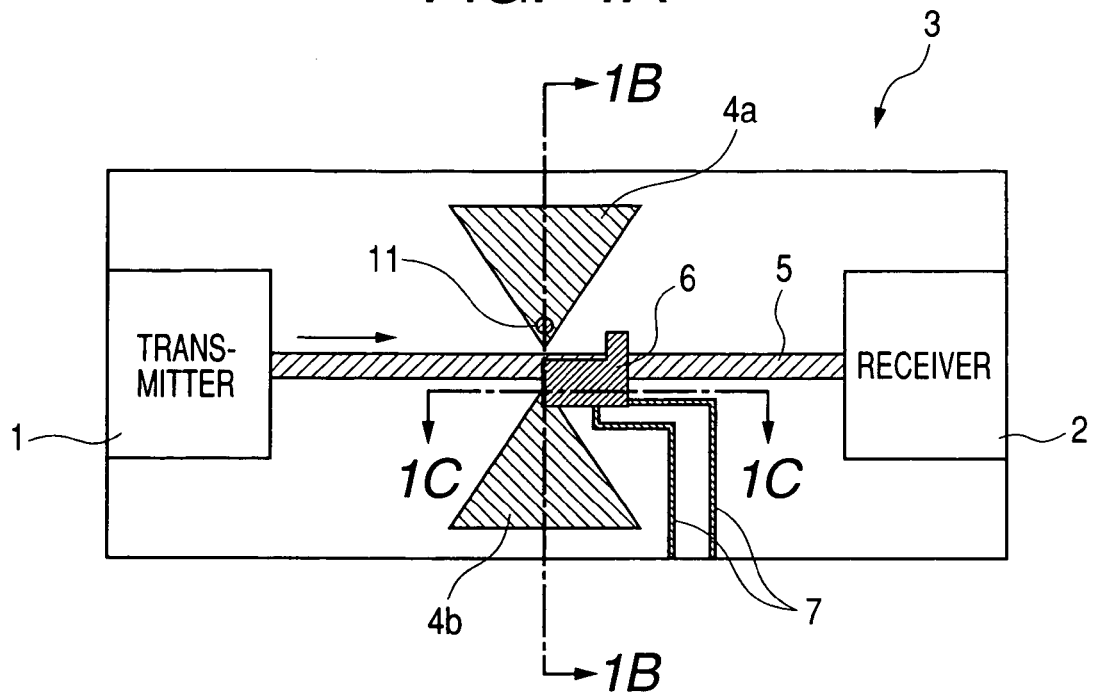
FIGS. 1A, 1B and 1C are views for explaining a construction of an integrated module of a first embodiment of a high frequency electrical signal control device according to the present invention.
Figure 1B:
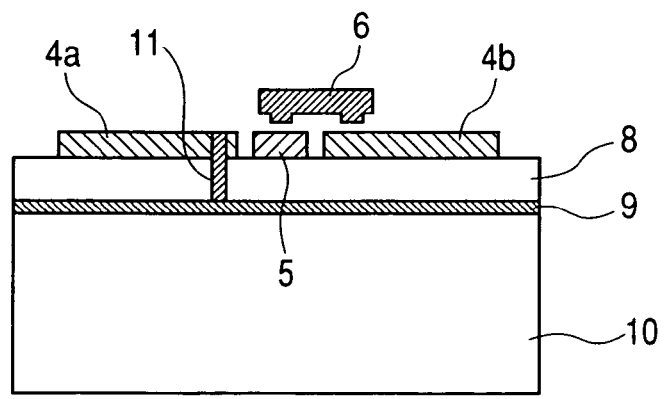
Figure 1C:
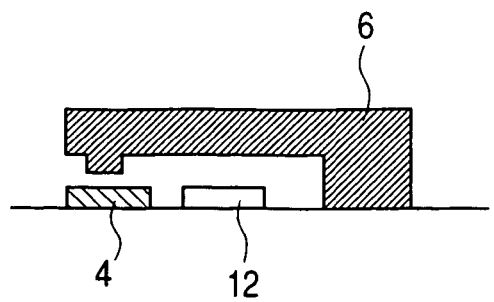

A first embodiment according to the present invention is shown in FIGS. 1A to 1C. In the first embodiment, as shown in FIG. 1A, bow tie type thin film antennas 4a and 4b are formed in the middle of a microstrip line 5 on the same module 3, and connection between the microstrip line 5 and the antennas is controlled with a miniature contact switch 6. While a transmitter 1 and a receiver 2, as shown in FIG. 1A, are integrated within the same module in a hybrid manner, there may be adopted a form in which the transmitter 1 and the receiver 2 are connected to an external transmitter or receiver. As for the transmitter, for example, an oscillation circuit for a microwave and a millimeter wave may be used in which a hetero-bipolar transistor (HBT) is used as an amplifier. A Schottky barrier diode (SBD) may be used as the high speed receiver. As shown in FIG. 1B shown as a cross sectional view taken along line 1B-1B of FIG. 1A, the microstrip line 5 is structured such that a ground plane 9 made of Ti/Au or the like is formed on a substrate 10, and the microstrip line (a transmission line pattern) 5 made of Ti/Au is formed on an insulator 8.

As for a material of the substrate 10, Si, glass ceramics, AlN or the like is suitably used. As for a material for the insulator 8, a material is suitable which is obtained by applying a BCB resin, polysilane, polyimide or the like on the substrate through a spin-coating process to cure the applied material. The pattern of the microstrip line 5 and the film antennas 4a and 4b can be simply formed on the insulator 8 by utilizing the lift-off method using the photolithography technique. Note that prior to formation of the film antennas 4a and 4b, a through hole electrode 11 is formed in order to obtain a contact with the ground plane 9. As for a contact switch 6, as shown in FIG. 1C shown as a cross sectional view taken along line 1C-1C of FIG. 1A, an electrostatic driving type switch having a cantilever structure is integrated. A voltage of 30 V is applied across driving wirings 7 so that an electrode 12 and the contact switch 6 attract each other by an electrostatic attracting force. As a result, the film antenna 4b, also shown in FIG. 1C as antenna 4. is connected to the microstrip line 5.

While the contact switch 6 is kept in a turn-OFF state, most of an output of the transmitter 1 reaches the receiver 2, and hence initial setting and the like can be carried out without sending the signal to the outside. Upon turn-ON of the contact switch 6, a part of the signal is emitted to the outside to be propagated through the air in accordance with reflection/transmission characteristics of the film antennas 4a and 4b. Then, a part thereof reaches the receiver 2, and another part thereof is returned back to the transmitter 1. In addition, an electromagnetic wave propagated from the outside or a return electromagnetic wave which is the reflection of the electromagnetic wave emitted from this module can be received by the film antennas 4a and 4b to be coupled to the microstrip line 5 to be received by the receiver 2. A rate of coupling between the film antennas 4a and 4b, and the microstrip line 5 can also be changed on the basis of a shape of the ground plane 9 disposed directly under the antennas.

Figure 2A:
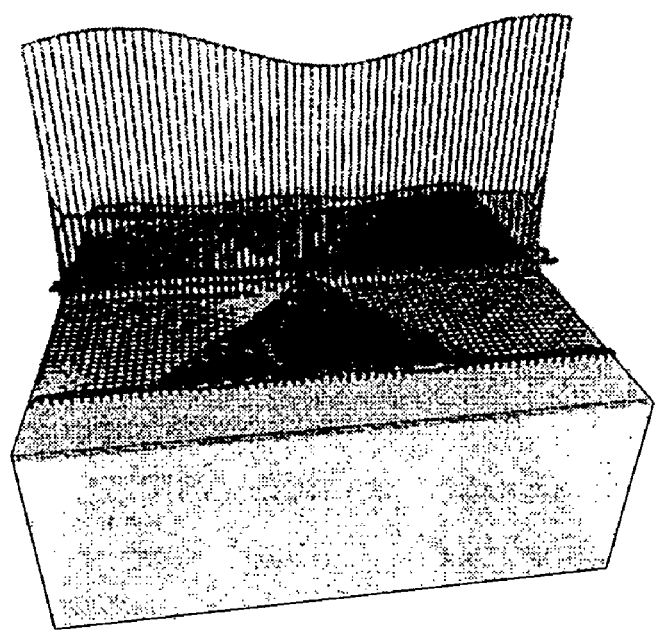
FIGS. 2A and 2B are views showing an electromagnetic wave analysis example when a switch is in a turn-OFF state in the first embodiment.
Figure 2B:
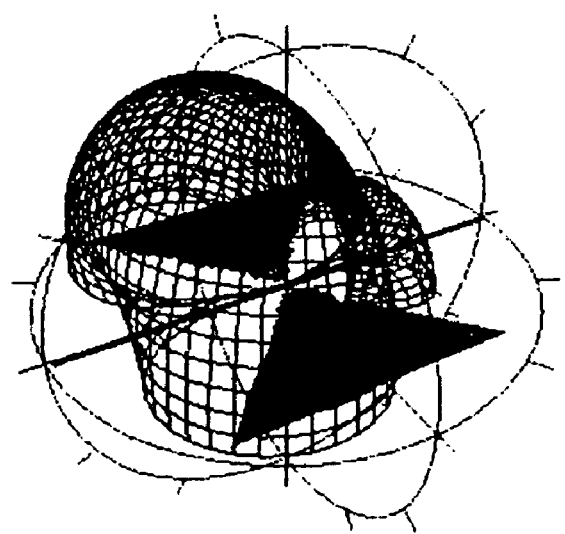
Figure 3A:
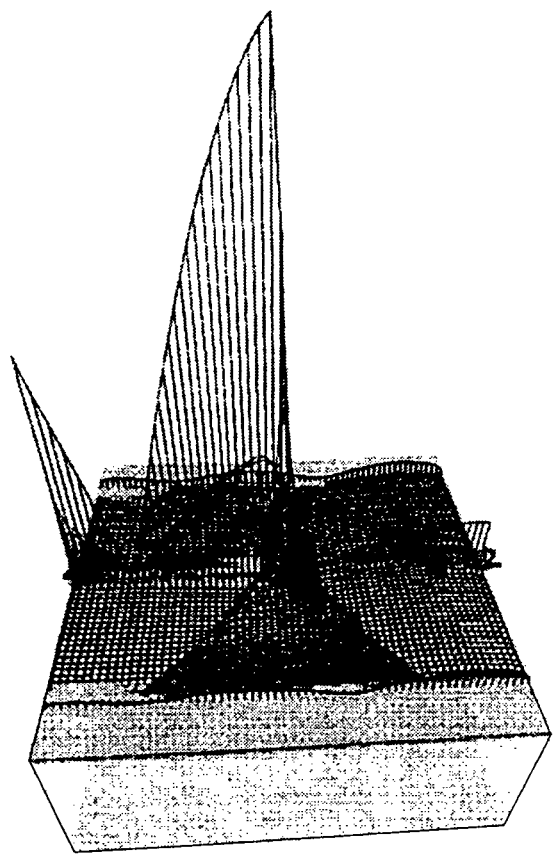
FIGS. 3A and 3B are views showing an electromagnetic wave analysis example when a switch is in a turn-ON state in the first embodiment.
Figure 3B:
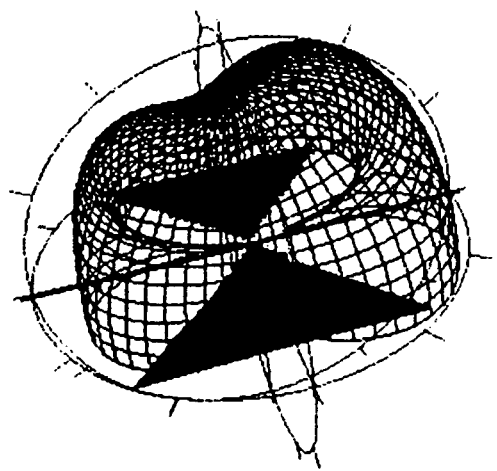

For the microstrip line pattern, the following design examples are possible. The Ti/Au (50 nm/450 nm) electrode 9 is formed on the Si substrate 10 which is 500 µm in thickness and 10 mm×25 mm in external size, and the microstrip line 5 with 25 µm width is further formed above the Ti/Au (50 nm/450 nm) electrode through the insulator (polysilane) 8 (its relative permittivity $\in_r$=2.8) with 10 µm thickness. In this case, a 50Ω matching line is obtained. Electromagnetic wave analysis examples of 100 GHz propagation when an isosceles right triangle having a base of 800 µm is adopted for a shape of each of the film antennas 4a and 4b are shown in FIGS. 2A and 2B, and FIGS. 3A and 3B. In these figures, the left-hand side corresponds to an input port, and the right-hand side corresponds to an output port. Each of them has 50Ω termination. FIGS. 2A and 2B show a state in which the contact switch 6 is held turned OFF. From a current distribution view of FIG. 2A, it is understood that nearly the whole signal reaches the output port on the right-hand side since no electric power is supplied to the film antennas 4a and 4b. FIG. 2B shows an antenna radiation pattern. From FIG. 2B, it is understood that there is some amount of asymmetrical leakage electric field. On the other hand, FIGS. 3A and 3B show a state in which the contact switch 6 is held turned ON. From FIG. 3A, it is understood that an electric power is supplied to the film antenna 4a and 4b, and hence the magnitude of a signal reaching the output port on the right-hand side is small. In addition, from FIG. 3B showing an antenna radiation pattern, it is understood that an electromagnetic wave having symmetrical directivity is radiated.

With the very miniature module (about 10 mm×about 25 mm in size in the above-mentioned numerical example) as described above, a state of coupling of the high frequency signal with the space can be changed by turning ON/OFF the contact switch 6 using the voltage signal. The module can be suitably used in a wireless module of a portable apparatus or the like to increase a degree of freedom of its design.

In this embodiment, the bow tie type antennas are used as an example. However, there may be used all the film antennas as will be described in the following embodiments as well, i.e., a dipole type antenna, a patch type antenna, a slot type antenna, a spiral type antenna, a log-periodic type antenna, or an antenna which is obtained by arranging a plurality of these antennas to obtain a broadband, a Yagi antenna, a horn antenna and the like. In particular, since it is necessary to obtain a broadband when a high frequency pulse is generated, an antenna of a type suitable for such a case may be used. In addition, there may be adopted a form in which GaAs or InP is used as a substrate material, and high speed electronic devices such as an HBT and an SBD are monolithically integrated.

Second Embodiment

Figure 4A:
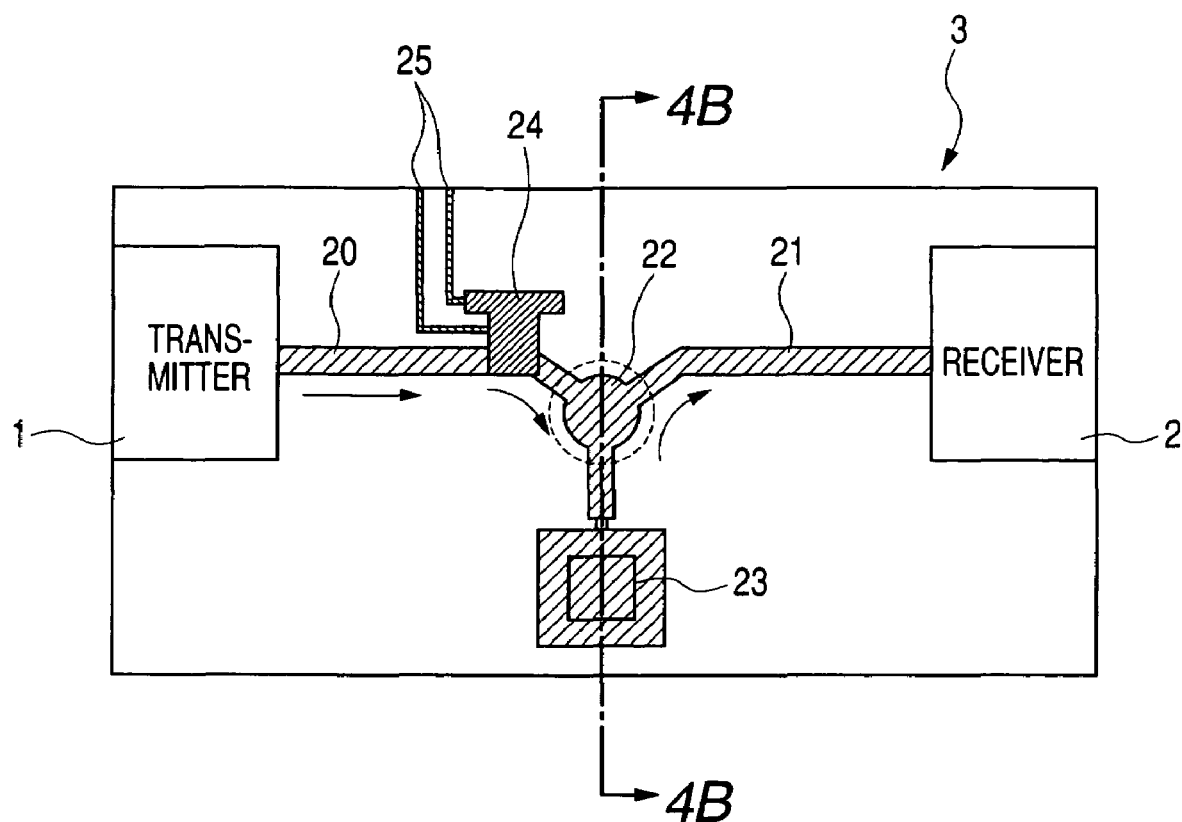
FIGS. 4A and 4B are views for explaining a construction of an integrated module of a second embodiment of the high frequency electrical signal control device according to the present invention.
Figure 4B:
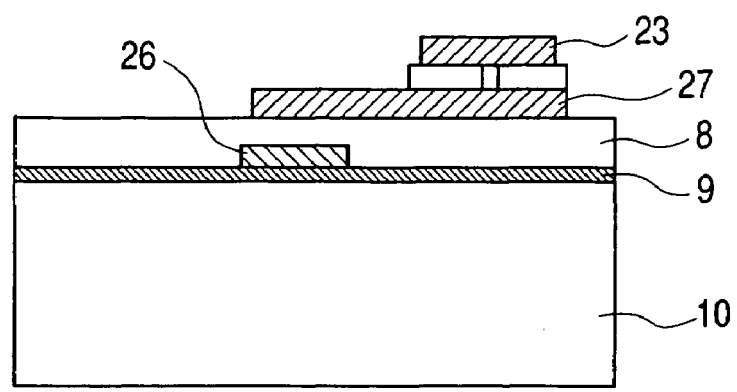

In the construction of the first embodiment, the signal control may not be carried out because the electromagnetic wave is reflected by the transmission line or the antenna depending on the frequency bands in some cases. Then, this embodiment aims at controlling flows of signals using circulators. FIGS. 4A and 4B show this embodiment in which a flow of a signal from a transmitter 1 to an antenna 23, and a flow of a signal from the antenna 23 to a receiver 2 are limited to one direction by circulators 22 and 26. The signal from the antenna 23 to the receiver 2 is a composite signal which is obtained by composing an electromagnetic wave generated through reflection of the signal from the transmitter 1 with an electromagnetic wave received from the outside. Note that a signal from the receiver 2 to the transmitter 1 is not illustrated since its magnitude is weak. This circulator, as shown in a cross sectional view of FIG. 4B, is structured by embedding a ferrite plate 26 in a circulator 22.

In this embodiment, double patch antennas 23 and 27 are adopted as the antennas for transmission/reception of the high frequency pulse to obtain a broadband. In this case, as shown in the cross sectional view of FIG. 4B, the patch antennas 23 and 27 which are different in size are vertically laminated and connected to each other. A structure of the antennas, as described in the first embodiment as well, is not limited to this structure. Transmission lines 20 and 21, similarly to the first embodiment, are formed as 50Ω matching lines, and a mechanical switch 24 for signal control is provided on the transmission line 20. The transmission line 20 is disconnected in this portion in which the mechanical switch 24 is provided, and its disconnected portion is closed/opened in accordance with turn-ON/turn-OFF of the switch 24. Similarly to the first embodiment, a suitable voltage is applied across electrodes 25 to turn ON/OFF the switch 24 to allow the radiation of the electromagnetic wave from the patch antennas 23 and 27 to be controlled. Other points are the same as those in the first embodiment.

Third Embodiment

Figure 5A:
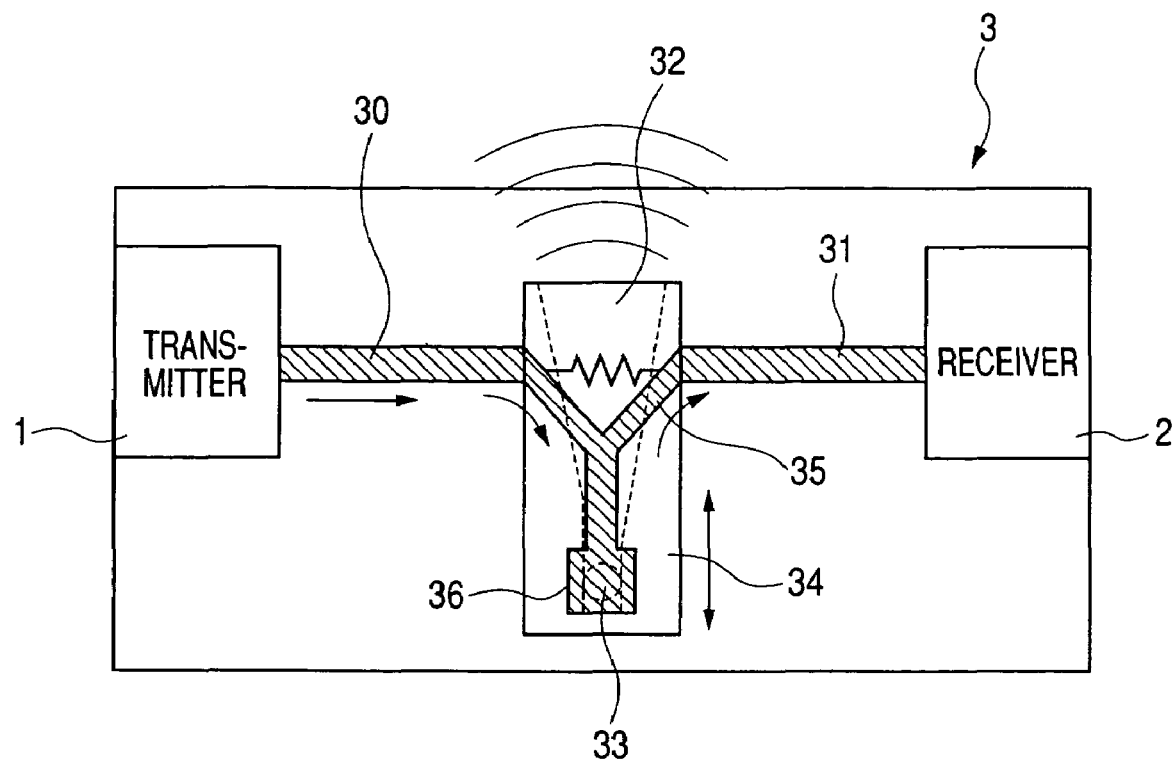
FIGS. 5A and 5B are views for explaining a construction of an integrated module of a third embodiment of the high frequency electrical signal control device according to the present invention.
Figure 5B:
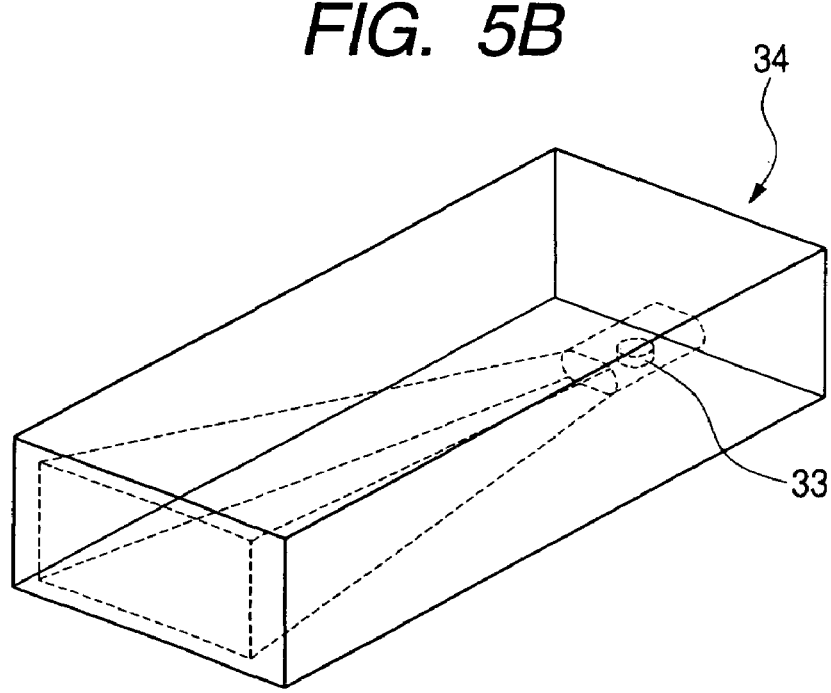

A construction of this embodiment is shown in FIGS. 5A and 5B. In the above-mentioned embodiments, only ON/OFF control is carried out for the radiation of the electromagnetic wave from the antennas, and the magnitude of the signal supplied to the antennas when the signal is radiated in the form of an electromagnetic wave is fixed. However, in this embodiment, a horn antenna 34 manufactured so as to be miniature is moved to control a degree of signal supply in order to change the intensity of a radiated electromagnetic wave or a received electromagnetic wave.

Transmission lines 30 and 31, a transmitter 1, and a receiver 2 are the same as those in the second embodiment. In addition, while in the second embodiment, the flows of the signals are controlled using the circulators, in this embodiment, only direct propagation of a signal from the transmitter 1 to the receiver 2 is limited using a directional coupler 35 and a resistor 32. Its isolation ratio can be controlled on the basis of a resistance value of the resistor 32, a shape of the directional coupler 35 and the like. In this case, a reflected component from the antenna is returned back to the transmitter. Therefore, in the case where this reflected component needs to be limited, these elements may be replaced with a circulator, or an isolator may be provided before the transmitter 1.

A primary radiator 36 having a patch antenna shape is provided in one termination of the directional coupler 35. A horn antenna 34 for radiating an electromagnetic wave from the primary radiator 36 to the space while the strong directivity is held is coupled to the primary radiator 36 through a hole 33. In this case, a waveguide structure may be formed within a substrate instead of the microstrip line, and a hole may be formed in a coupling portion with the horn antenna 34.

The horn antenna 34, as shown in FIG. 5B, has such a structure as to have a hollow portion having a horn shape inside a block-like body. In actual, two structures are prepared each of which is formed by depositing Au or the like onto an inner wall of a resin or Si structure manufactured through a surface process by utilizing a vacuum evaporation method. Then, the two structures are stuck to each other to form the horn antenna 34. If this horn antenna 34, as shown in FIG. 5A, is designed so as to be movable on an integrated module 3 (in a direction indicated by a double-headed arrow), then an efficiency of coupling with the primary radiator 36 through the hole is changed. As a result, it is possible to modulate the intensity of the electromagnetic wave radiated from the antenna 34, or the sensitivity at which the electromagnetic wave can be received by the antenna 34. As a method including driving the block-like antenna 34, an electrostatic method, an electromagnetic method using a magnet, an ultrasonic wave method or the like is suitably used. In addition, if the rotation of the horn antenna 34 around the hole 33 is controlled, then the beam direction of the electromagnetic wave can be deflected while a degree of coupling is held nearly fixed.

Fourth Embodiment

Figure 6:
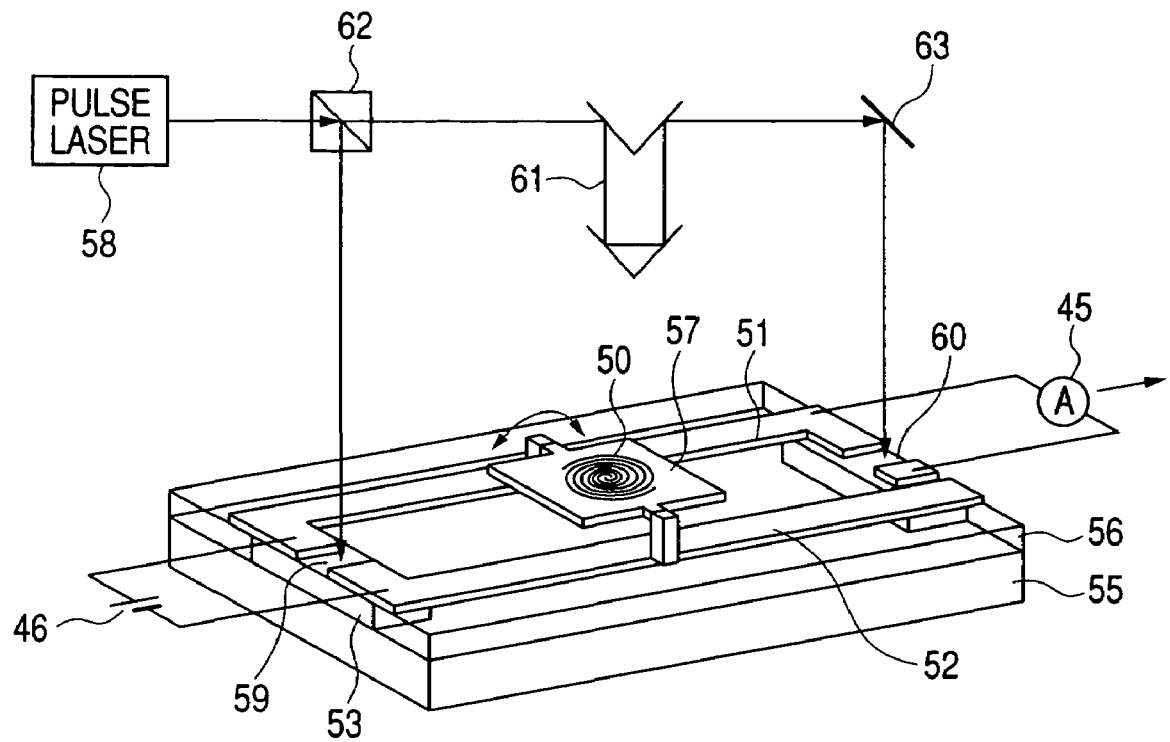
FIG. 6 is a perspective view for explaining a construction of an integrated module of a fourth embodiment of the high frequency electrical signal control device according to the present invention.

A fourth embodiment according to the present invention is such that, as shown in FIG. 6, a spiral antenna 50 is formed on a dielectric structure 57 supported by a pair of torsion springs or the like so as to be able to be driven rotationally around an axis of the torsion springs or the like, and the beam scanning is carried out using this spiral antenna 50. A transmission line, a transmission circuit and a reception circuit may be the same as those in the above-mentioned embodiments. In this embodiment, however, there is used a co-planar strip line in which two conductors 51 and 52 are formed on a surface of an insulating layer 56 formed on a substrate 55 to allow push-pull driving to be carried out.

Figure 7A:
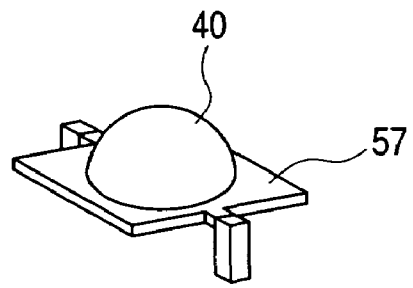
FIGS. 7A and 7B are perspective views showing examples of controlling directivity of an electromagnetic wave beam in the integrated module of the fourth embodiment according to the present invention.
Figure 7B:
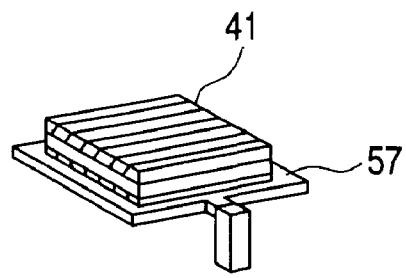
Figure 8:
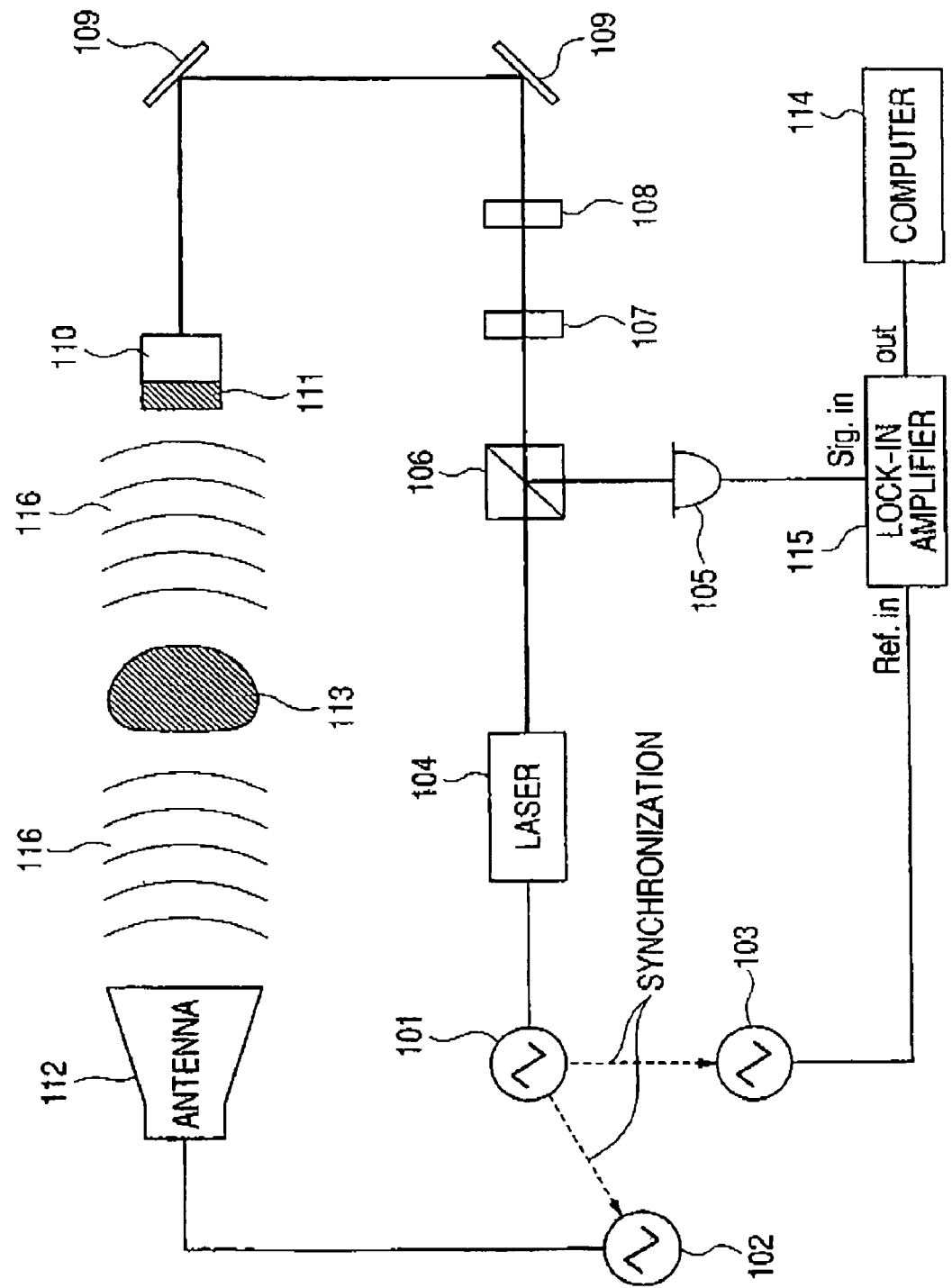
FIG. 8 is a diagram showing a conventional example of a millimeter wave two-dimensional imaging system.
Figure 9:
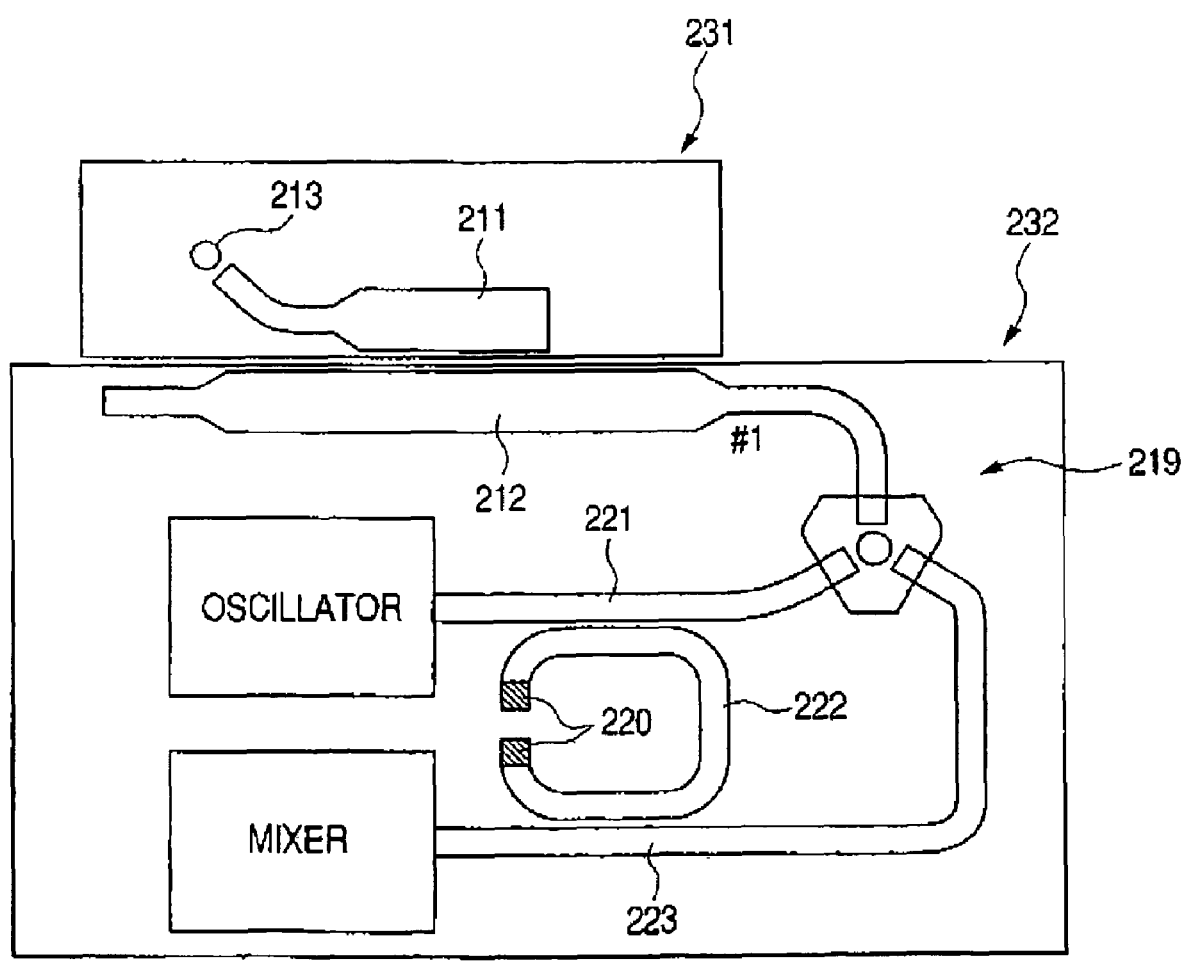
FIG. 9 is a diagram showing a conventional example of a transmission/reception unit of a millimeter wave radar system.

An electric power which is to be supplied to the spiral antenna 50, as shown in FIG. 6, is obtained from the conductors 51 and 52 through a rotation driving support portion of the dielectric structure 57. The dielectric structure 57 can be vibrated at a specific frequency by utilizing an electromagnetic driving method and the like, and carries out the scanning with a beam of an electromagnetic wave from the spiral antenna 50. At this time, when the directivity is wanted to be enhanced, as shown in FIG. 7A, a semi-spherical lens 40 made of Teflon, Si, and the like has to be further integrated on the dielectric structure 57. Or, if a photonic crystal 41 is integrated as shown in FIG. 7B, then it is possible to obtain a beam having very high directivity due to a spar collimate effect. The photonic crystal 41 can be realized in the form of a structure in which a plurality of layers each having Si rod rows are laminated so that the Si rod rows of the layers formed in lines each having a width on the order of a wavelength (e.g., about 1 mm) are perpendicular to one another.

In addition, for transmission and reception of a high frequency pulse signal, there may be adopted a method in which a photoconductive switch 59 is turned ON/OFF using a short pulse laser 58. That is, there is utilized a phenomenon that while an undoped GaAs layer 53 formed through a low temperature growth has normally a high resistance, only at a moment when a laser beam is applied to a gap of the photoconductive switch 59, photo carriers are generated in the undoped GaAs layer 53, and if a voltage 46 is applied across both ends of the gap, a current is caused to flow in an instant to generate a high frequency pulse. If a width of the pulse from the pulse laser 58 is set to about 100 fsec, this pulse can be converted into an electromagnetic wave pulse having a pulse width of about 0.4 psec, and this results in that an electromagnetic wave having a frequency ranging over a THz region is radiated. As for the pulse laser 58, a mode lock laser made of titanium sapphire is easy to handle since it has high controllability. However, in a case where portability is regarded as important, a semiconductor mode lock laser may be used from a viewpoint of miniaturization.

On a reception side, the high frequency pulse propagated through the conductors 51 and 52 is received by a photoconductive switch 60 having the same structure as that of the photoconductive switch 59. At this time, the laser beam reflected by a reflecting mirror 63 after beam separation in a beam splitter 62 is applied to a gap as well of the photoconductive switch 60 on the reception side so that only for a period of time when the laser beam is applied, a signal of the high frequency pulse can be observed in the form of a current 45. In order to separate a D.C. voltage on a side of generation of the high frequency pulse, the photoconductive switch 60 is separated from one conductor 52 of the co-planar strip line.

Here, an amount of delay of the short pulse laser beam is controlled by an optical delay unit 61, whereby a signal waveform of the high frequency pulse can be observed while this signal waveform is sampled. If a voltage developed across the photoconductive switch 59 on the side of generation of the high frequency pulse is modulated with a sine-wave signal to be synchronously detected on the reception side, then the high sensitivity measurement becomes possible. In this embodiment as well, the mechanical switch described in the first embodiment may be integrated in a portion of one of the lines 51 and 52 between the photoconductive switch 59 and the spiral antenna 50 to carry out ON/OFF control for a signal.

Such transmission/reception using an electrical pulse is in a progress of being developed in a wireless sensing system, high speed communication and the like as a broadband wireless technique, i.e., a so-called ultra-wide band (UWB) technique. The controller of the present invention is effectively applied to such a UWB system.

In each of the above-mentioned embodiments, the structure of the miniature integrated module for carrying out the sensing or the like using the electromagnetic wave ranging from a millimeter wave to a terahertz wave has been described. This integrated module can be applied as a device more excellent in portability to a field of two-dimensional transmission or reflection imaging of a substance, a short distance position sensing radar or the like as explained in the related art example. In a case where this device is utilized as the imaging device, a system capable of easily carrying out inspection anywhere without requiring an installation space can be provided as a system for security check of person's belongings, a system for inspecting an IC card, a fingerprint sensor, or a medical care diagnosis system for diagnosing a blood stream, a skin, eyes and the like. In addition, in a case where this device is used as the position sensing device as well, this device can be provided in the form of being incorporated in a portable apparatus, and hence can be applied to a wireless input unit for a display device, a computer or the like, a remote control device, or a pointing device for a game or the like.

Fifth Embodiment

Figure 10:
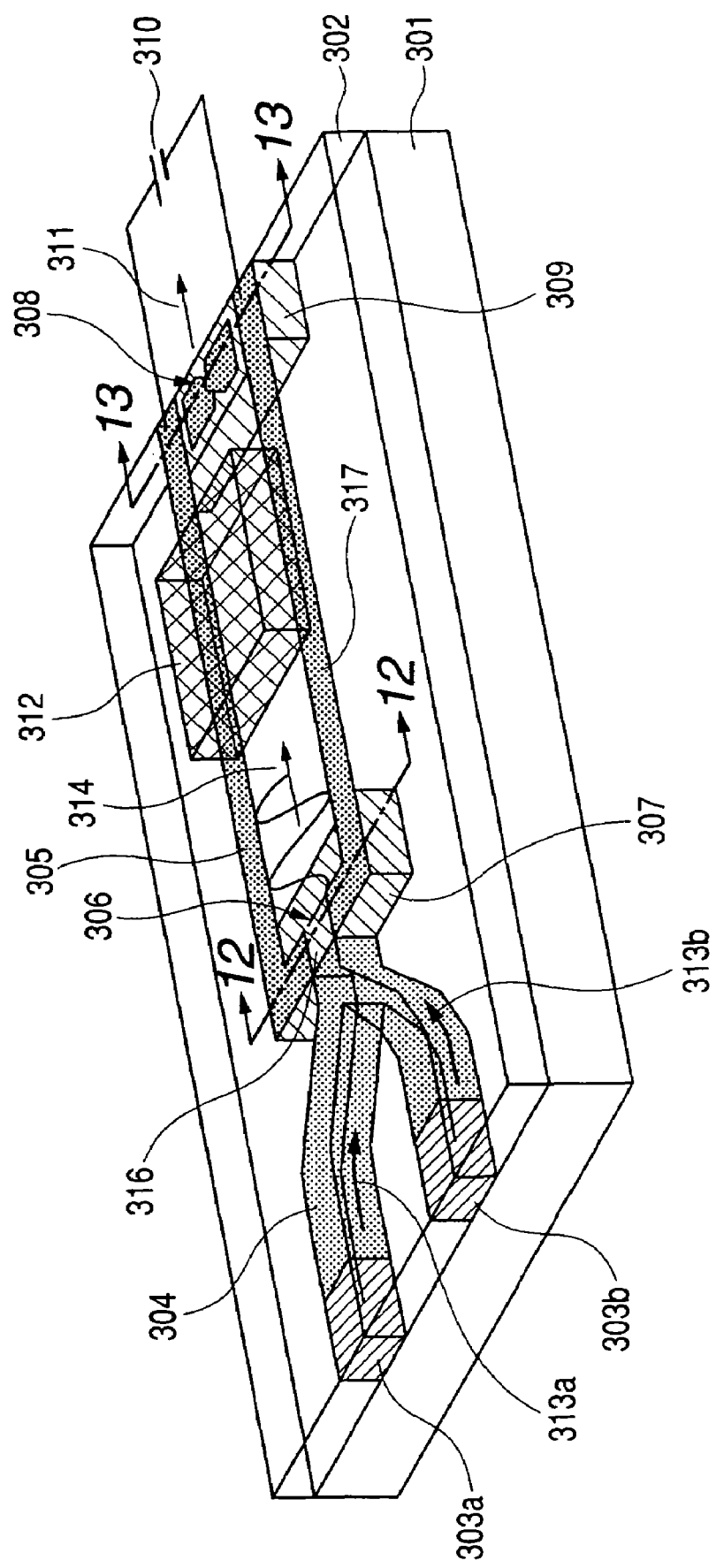
FIG. 10 is a perspective view of a construction of an integrated module of a fifth embodiment according to the present invention.

A fifth embodiment according to the present invention is such that two semiconductor lasers for carrying out two-wavelength mixing, an optical waveguide, a terahertz generator, a transmission line through which a terahertz wave is propagated, and a terahertz detector are integrated on one substrate, i.e., mounted on a common substrate. A perspective view of this integrated module is shown in FIG. 10.

An insulating resin 302 having photosensitivity is formed on a semi-insulating GaAs substrate 301. A refractive index of only an area of the insulating resin 302 corresponding to a Y-branch optical waveguide 304 is larger than that of the peripheral area through the photolithography process. As a material of this insulating resin 302, for example, photosensitive polysilane (trade name: Glasia (manufactured by NIPPON PAINT CO. LTD.)) is suitably used. In addition to this material, an optical resin having photosensitivity such as BCB or polyimide is suitable for a layer serving both as an optical waveguide and an electrical insulating layer.

AlGaAs/GaAs series distribution feedback (DFB) type semiconductor lasers 303a and 303b are mounted in hybrid manner. Each of the semiconductor lasers 303a and 303b can carry out single mode oscillation, and has a multi-electrode structure. Thus, with each of these semiconductor lasers 303a and 303b, a wavelength can be continuously changed by about 2 nm without largely changing an optical output. There should be used an element which has different diffraction grating pitches so that oscillation center wavelengths of the two semiconductor lasers 303a and 303b previously differ from each other by about 1 THz. Moreover, a difference between oscillation wavelengths of the two semiconductor lasers 303a and 303b is stabilized by detecting a part of a beam to carry out feedback control using an injected current. In a wavelength band (830 nm band) of these semiconductor lasers 303a and 303b, a conversion factor between a wavelength and a frequency is about $4.35 \times 10^{11}$ (Hz/nm). For generation of a beat frequency of 1 THz, a wavelength difference of about 2.3 nm has to be given. As the feedback control for the wavelength concerned, for example, in phase locked loop (PLL) control, offset lock using a frequency divider and a synthesizer has to be made. Since an amount of offset corresponds to the beat frequency, a generated frequency of an electromagnetic wave is determined by the synthesizer. While in principle, all beat frequencies can be generated, giving consideration to a lock range and a spectral line width (about 10 MHz) of the semiconductor laser, it is judged that the beat frequency falls within a range of several tens of MHz to about 10 THz. In this embodiment, continuous tune from 100 GHz to 3 THz is carried out.

Laser beams emitted from the respective semiconductor lasers 303a and 303b are propagated in the form of propagated beams 313a and 313b to be applied to a terahertz generator 306 through a photoconductive switch. At this time, since the propagated beams 313a and 313b are propagated through the Y-branch optical waveguides 304 overlying the substrate 301, polarization in the laser beams emitted from the semiconductor lasers 303a and 303b is held. As a result, no polarization adjusting means is required. The photoconductive switch is constituted by a film 307 which is formed through low temperature growth (at about 20° C.) of undoped GaAs, and normally has excellent insulating property. Hence, even if about 30 V is applied from a D.C. voltage source 310 to two conductors 305 and 317, no current is caused to flow through the photoconductive switch. Upon application of the laser beam, photo carriers are generated to cause a current to flow through the photoconductive switch. In this case, the photo carriers are modulated with the above-mentioned beat frequency to generate an electromagnetic wave 314 corresponding to the beat frequency. The electromagnetic wave 314 is propagated through the conductors 305 and 317 formed on the insulating resin 302. At this time, it is supposed that for example, a width of each of the conductors 305 and 317 is 30 μm, and an interval of the conductors 305 and 317 is 200 μm. Note that a width of a gap portion 316 of the terahertz generator 306 is supposed to be 5 μm.

Figure 12:
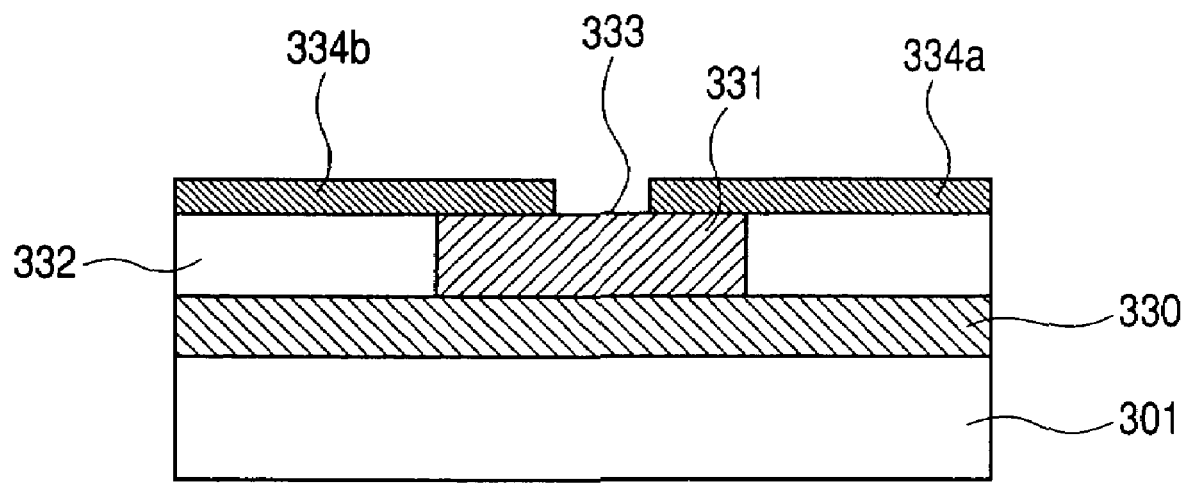
FIG. 12 is a cross sectional view of an example of a terahertz generator.

A cross sectional view taken along line 12-12 of another form of the photoconductive switch is shown in FIG. 12. In order to adopt a waveguide type for the photoconductive switch to enhance light absorption efficiency, an AlGaAs (composition of Al is 0.3) layer 330 and an undoped GaAs layer 331 are grown in this order on the substrate 301. Then, the GaAs layer 331 is selectively etched away in a width of about 10 μm, and an insulating layer 332 is then buried on both sides of the resultant GaAs layer 331. In addition, electrodes 334a and 334b are provided so as to face each other through a gap 333. Conversion efficiency in this form is enhanced as compared with the case of provision of the GaAs bulk layer 307 as shown in FIG. 10. Also, as still another form, the efficiency of generation of the electromagnetic wave 314 based on the beat frequency may be enhanced by using a nonlinear crystal.

Figure 13:
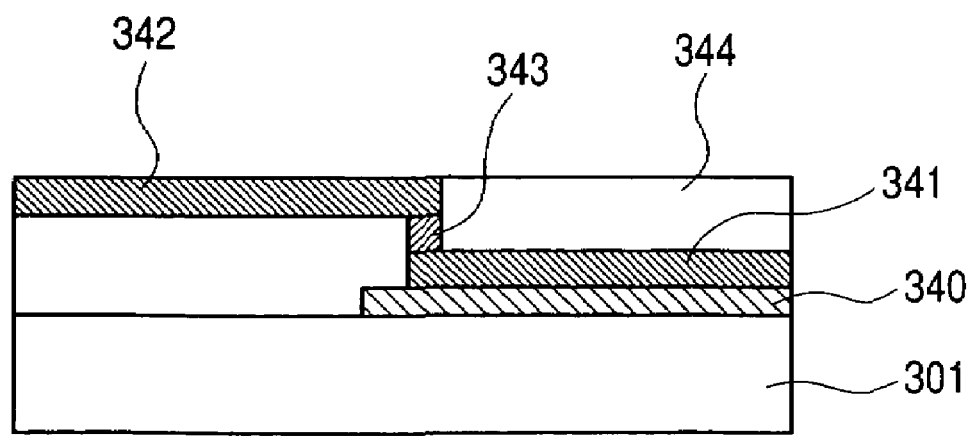
FIG. 13 is a cross sectional view of an example of a terahertz detector.

The propagated terahertz wave 314 is obtained in the form of an electrical signal 311 by a detector 308 (illustrated as being formed on the semiconductor layer 309 in FIG. 10). A Schottky barrier diode as shown in FIG. 13 as a cross sectional view taken along line 13-13 of FIG. 10 is used as a detector 308. This Schottky barrier diode includes an AuGe/Ni/Au electrode 341 formed on an n-type GaAs layer 340 grown on a semi-insulating GaAs substrate 301, a point contact portion 343 formed as a through hole electrode with a diameter equal to or smaller than 2 μm, a Schottky electrode 342, and an insulating layer 344. Each of the Schottky electrode 342 and the point contact portion 343 is made of Ti/Pt/Au. A frequency ranging over about 1 THz can be detected with the detector 308. Note that as shown in FIG. 10, the conductors 305 and 317 are separated from the electrode 308.

A specimen 312 as a sensing object is placed on the integrated module having the above-mentioned construction (its length and width are on the order of about millimeter). While the terahertz wave 314 is propagated through the conductors 305 and 317, the electromagnetic wave (evanescent wave) leaks to the surface as well. As a result, the intensity of the millimeter wave or the terahertz wave detected by the detector 308 is changed in correspondence to the absorption characteristics of the specimen 312. Consequently, the specimen is measured while the beat frequency is changed to allow the spectrochemical analysis of the terahertz region of the specimen 312 to be carried out. The frequency resolving power in the spectral diffraction is determined by a spectral line width of a used laser, and is about 10 MHz in this embodiment. As for the specimen 312, any substances such as semiconductors, metal, dielectric, organic materials, living body substances (cells, DNA, and protein), foods and plants become sensing objects. Thus, it is possible to simply examine the characteristics of the terahertz region, with respect to any substances, which could not be conventionally obtained.

When the measurement is actually carried out, in order to enhance an S/N ratio, there may be adopted a process in which a sine-wave signal with a frequency equal to or lower than 1 MHz is superimposed on the signal from one of the semiconductor lasers, and on the detector 308 side as well, the signal is mixed with the signal from the same signal source to carry out the synchronous detection.

Figure 11A:
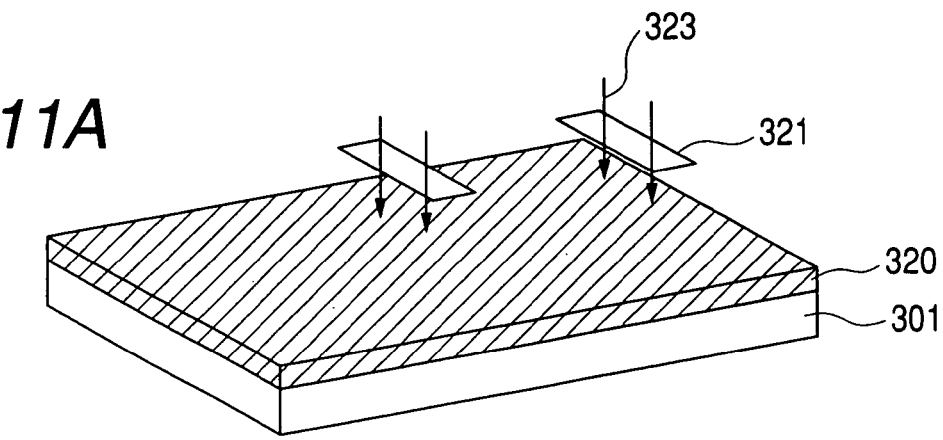
FIGS. 11A, 11B, 11C and 11D are diagrams for explaining processes in a method including manufacturing the integrated module of FIG. 10.
Figure 11B:
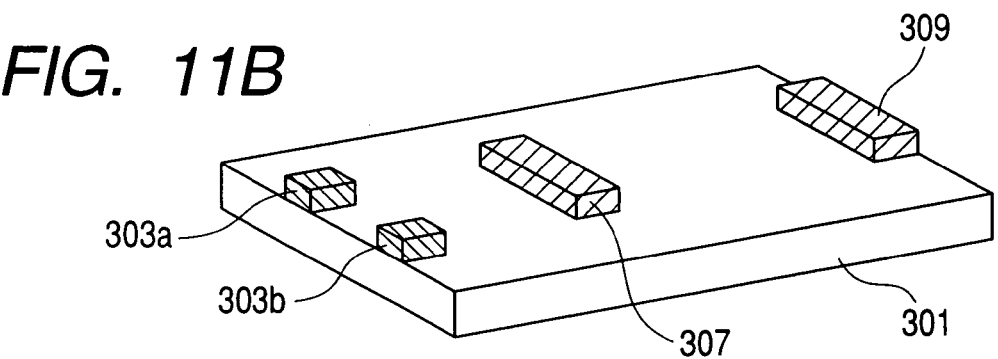

An example of a method including manufacturing this module is shown in FIGS. 11A to 11D. In FIG. 11A, a GaAs layer 320 made of a GaAs crystal is grown on the semi-insulating GaAs substrate 301. At this time, if necessary, the GaAs layer 320 may be grown heterogeneously with AlGaAs, or may be selectively grown plural times while the growth temperature and composition are changed depending on areas. In this case, the undoped GaAs layer which is to be formed through the low temperature growth and which is to constitute the photoconductive switch is finally grown. Thereafter, resist patterning (not shown) is carried out with a photo mask having a pattern 321 through the photolithography process by applying a g-line 323 or the like. In FIG. 11B, induced coupled plasma (ICP) etching using chlorine is carried out with the photo resist as a mask to form the areas of the semiconductor layers 307 and 309. On the other hand, the two semiconductor lasers 303a and 303b are mounted to the predetermined positions, respectively.

Figure 11C:
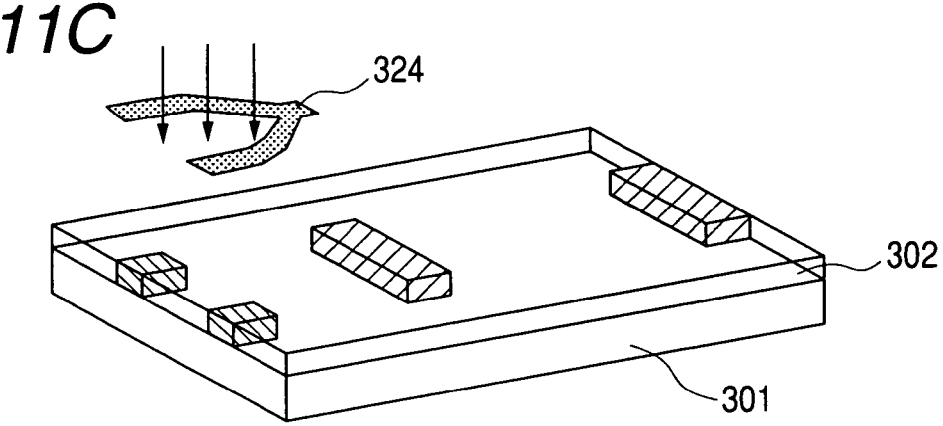
Figure 11D:
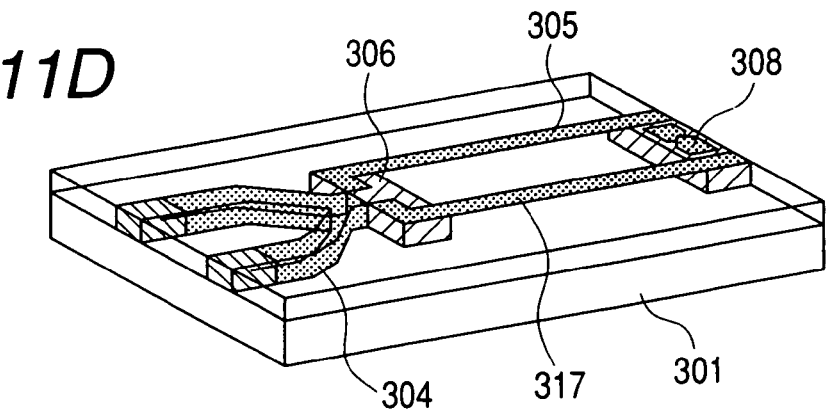

In FIG. 11C, the insulating resin (polysilane) 302 is applied to form the light-transmissive insulating layer, and i-line exposure is then carried out for an area in which the optical waveguide 304 is intended to be formed using a mask pattern 324. As a result, the optical waveguide 304 is formed since a refractive index difference of about 0.01 is generated in the area of the optical waveguide 304. In FIG. 11D, the electrodes made of Ti/Au are formed by utilizing the lift-off method to complete the module.

In such a manner, the optical waveguide 304 and the insulating resin 302 for the electromagnetic wave transmission are made of the same material, whereby it is possible to provide the integrated module which is relatively inexpensive and which is excellent in mass production. While in this embodiment, the co-planar strip line is used as the transmission line for the electromagnetic wave, all integration type transmission lines such as a microstrip line and a co-planar line can be applied.

Sixth Embodiment

Figure 14:
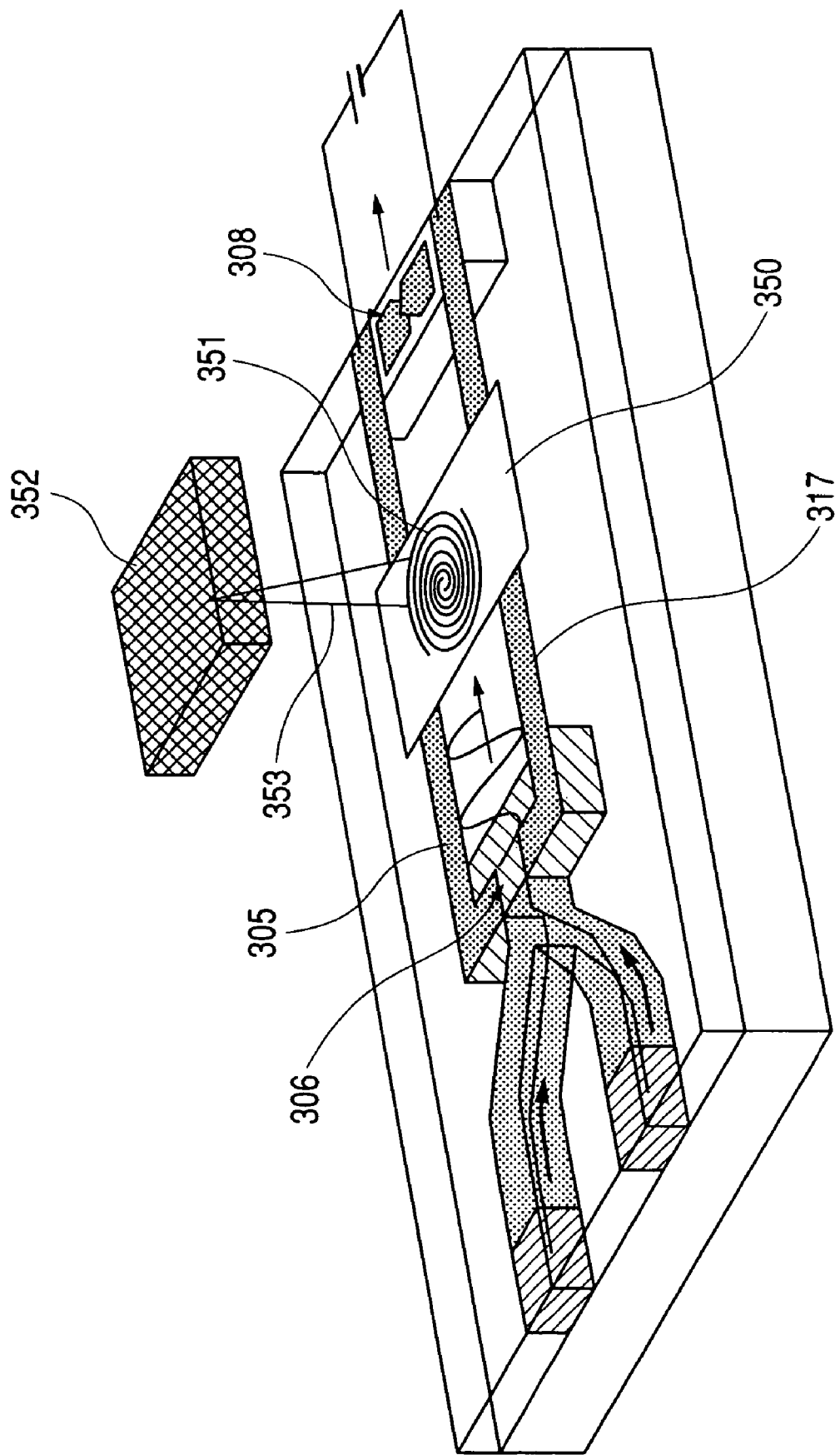
FIG. 14 is a perspective view of a construction of an integrated module of a sixth embodiment according to the present invention.

A sixth embodiment according to the present invention, as shown in FIG. 14, includes a spiral antenna 351 for radiating an electromagnetic wave ranging from a millimeter wave to a terahertz wave to the space so that a specimen 352 located spatially at a distance from the integrated module can be inspected.

A construction of the whole integrated module is nearly the same as that of the fifth embodiment. Thus, the mixing is carried out using two semiconductor lasers, and a terahertz generator 306 for converting an inputted electromagnetic wave into an electromagnetic wave corresponding to a beat frequency, the conductors 305 and 317, a detector 308, and the like are integrated. A spiral antenna 351 is formed in a dielectric structure 350 adapted to be vibrated and a direction of a beam 353 radiated to the space is adapted to be deflected if necessary. In addition, a mechanical switch (not shown) may be provided so as to be able to select whether or not an electric power is supplied from the conductors 305 and 317 to the spiral antenna 351. A reflected wave of the electromagnetic wave applied to the specimen 352 is received by the spiral antenna 351 again to obtain a signal by the detector 308.

If the structure 350 having the spiral antenna 351 placed thereon is set so as to be able to be one-dimensionally vibrated, the beam scanning can be carried out and hence a two dimensional reflection image of the specimen 352 can be obtained while the specimen 352 is moved in a direction intersecting perpendicularly the scanning direction. At this time, in order to enhance the directivity of the electromagnetic wave to enhance the spatial resolution of the image, a dielectric lens or a photonic crystal (not shown) may be further placed on the spiral antenna 351. As a result, since the spatial resolution on the order of a wavelength can be obtained, the spatial resolution becomes about 300 µm in case of an electromagnetic wave with a frequency of 1 THz. In order to further enhance the resolution, if a miniature opening having a size equal to or smaller than $\frac{1}{10}$ of a wavelength, i.e., an opening having a size equal to or smaller than 30 µm is formed in the above-mentioned lens or photonic crystal using metal or the like, this opening functions as a near-field probe. As a result, an image is obtained through the resolution of about a size of the opening. However, when this near-field probe is used, it is necessary to inspect the specimen 352 in a state in which the specimen 352 is close to the lens or photonic crystal.

In such a manner, in this embodiment, the specimen 352 can be inspected in a non-contact manner. In actual, since a terahertz wave is greatly attenuated (about 100 dB/km) while being propagated through the air, the inspection for a specimen having a size equal to or smaller than several meters is practical.

In this case, while there is given the example in which all the generation and detection of the electromagnetic wave ranging from a millimeter wave to a terahertz wave are processed using one module, the generator and the detector may be provided in the form of separate modules. In this case, a transmission two-dimensional image of the specimen can be obtained with the generator and the detector disposed so as to face each other.

Seventh Embodiment

In a seventh embodiment according to the present invention, a terahertz CW beam is not generated with a mixing beam, but an impulse having frequencies ranging over a terahertz region is generated to carry out time domain spectroscopy (TDS).

Figure 15:
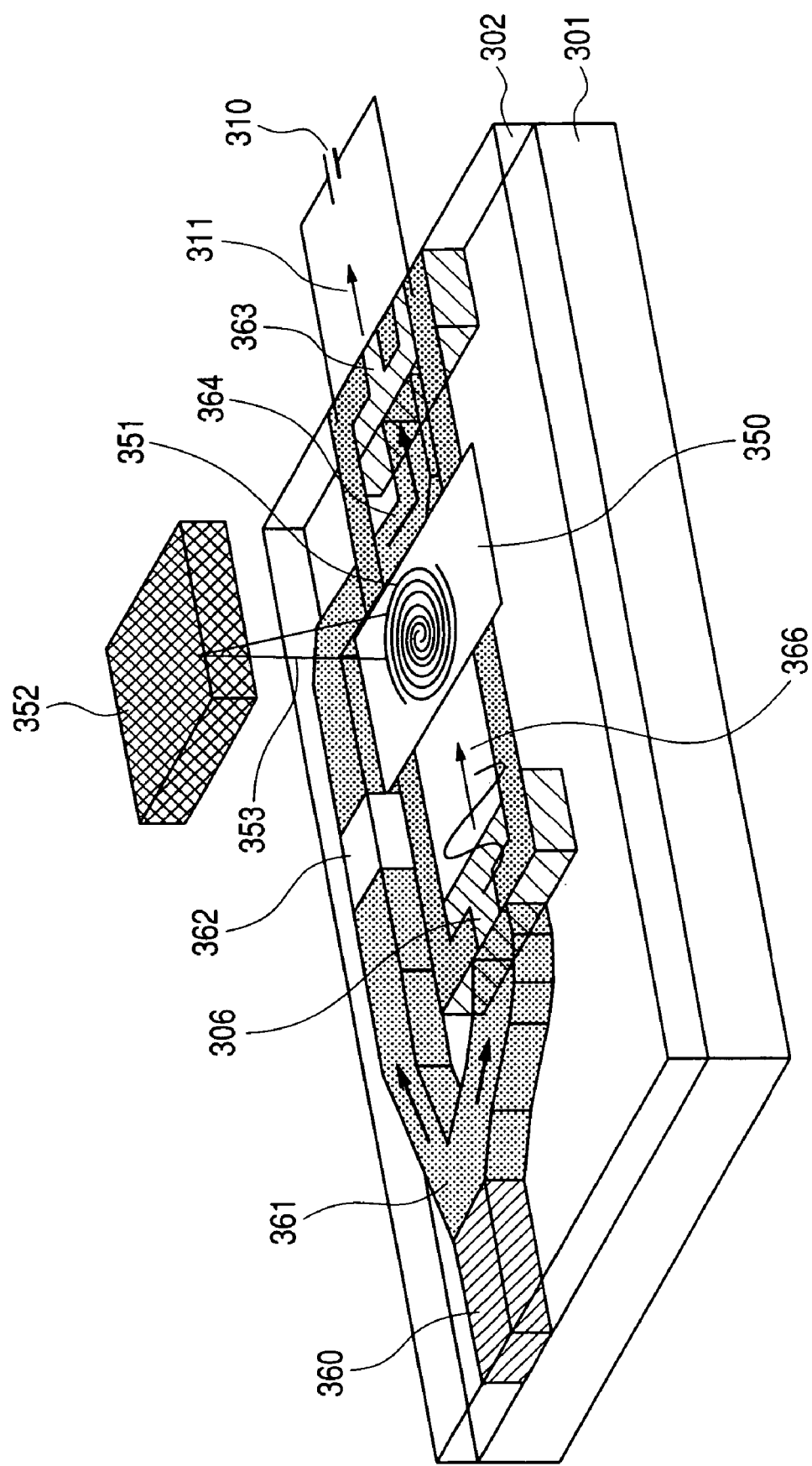
FIG. 15 is a perspective view of a construction of an integrated module of a seventh embodiment according to the present invention.

A construction of an integrated module is shown in FIG. 15. A semiconductor mode lock laser 360 is mounted on a substrate 301, and a pulse with a width of about 0.3 psec is emitted from the semiconductor mode lock laser 360 to be coupled to an optical waveguide 361. One of the propagated laser beams is applied to a terahertz generator 306 to be converted into an electromagnetic wave 366 with a pulse width of about 0.5 psec which is in turn propagated through a transmission line. The other of the laser beams obtained through branch in the optical waveguide 361, as indicated by a reference numeral 364, is applied to a detector 363 through an optical delay unit 362. The optical detector 363 is a photoconductive switching element having the same structure of the terahertz generator 306. Thus, in the optical detector 363, only at timing when a laser pulse is applied thereto, photo carriers are generated, and hence a current is caused to flow in correspondence to the magnitude of an electric field of the electromagnetic wave pulse propagated through the transmission line to be detected in the form of a signal. Consequently, an amount of delay in the delay unit 362 is changed to thereby be able to measure a time change of the electric field strength of the terahertz pulse. The delay unit 362 can be constituted by a delay waveguide and an optical switch (not shown), an element for changing a refractive index and the like. As for a detection method, in addition to the method in this embodiment, there may also be adopted a method in which an EO crystal is provided before the optical detector 363 to change a time fluctuation of the terahertz pulse strength into a fluctuation based on a Pockels effect of the EO crystal, and transmitted beam intensity of the beam obtained through the branch of the laser beam from the pulse laser is measured by the optical detector 363.

In this embodiment as well, as in the sixth embodiment, the electromagnetic wave pulse is radiated from the spiral antenna 351 to the space to measure the reflected electromagnetic wave from the specimen 352 to check up the impulse response, whereby carrier concentration, permittivity, mobility and the like in the inside of the specimen 352 can be inspected in a non-contact manner. The transmission measurement may also be carried out with two modules of the generator and the detector disposed so as to face each other. These methods are suitable for evaluation of semiconductors, especially, organic semiconductors, and electrically conductive polymeric films. If the specimen is scanned with the beam as in the sixth embodiment, then the two-dimensional distribution in the specimen is also examined. Also, if the delay time is measured, then highly accurate remote position sensing for the specimen also becomes possible. When a width of the terahertz pulse is 0.5 psec, if it is supposed that an amount of delay of about half the pulse width can be detected, then a position in the specimen can be detected with accuracy of $0.5 \times 10^{-12}/2 \times (3 \times 10^8) = 750$ µm.

When these TDSs are carried out, if an amount of beam delay is changed on the order of μsec to successively carry out trace while the synchronous detection as described in the fifth embodiment is carried out, a high speed electronic circuit may not be necessarily used.

Eighth Embodiment

In the above-mentioned embodiments, the description has been given with respect to the construction of the miniature integrated module for carrying out the sensing using the electromagnetic wave ranging from the millimeter wave to the terahertz wave. This integrated module can be applied as a device which is more excellent in portability such as two-dimensional transmission or reflection imaging device for inspecting a substance, or a short-distance position sensing radar as described in the related art example. In a case where this integrated module is utilized as the imaging device, a system capable of simply carrying out inspection anywhere without requiring an installation space can be provided as an inspection system for security check of person's belongings or for inspection of an IC card, a fingerprint sensor, or a medical care diagnosis system for diagnosing a blood stream, a skin, eyes or the like. In addition, in a case as well where the integrated module is used for the position sensing, the integrated module can be provided in the form of being incorporated in a portable apparatus. Hence, the integrated module can be applied to a wireless input unit for a display device or a computer, a remote control device, or a pointing device for a game, or the like.

Figure 16A:
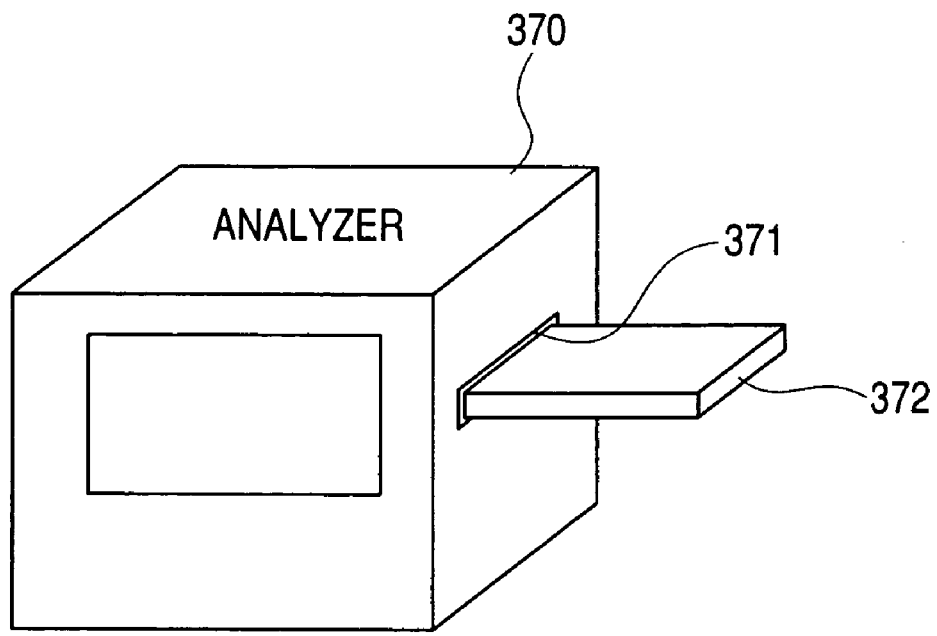
FIGS. 16A and 16B are perspective views for explaining a sensing system of an eighth embodiment according to the present invention.
Figure 16B:
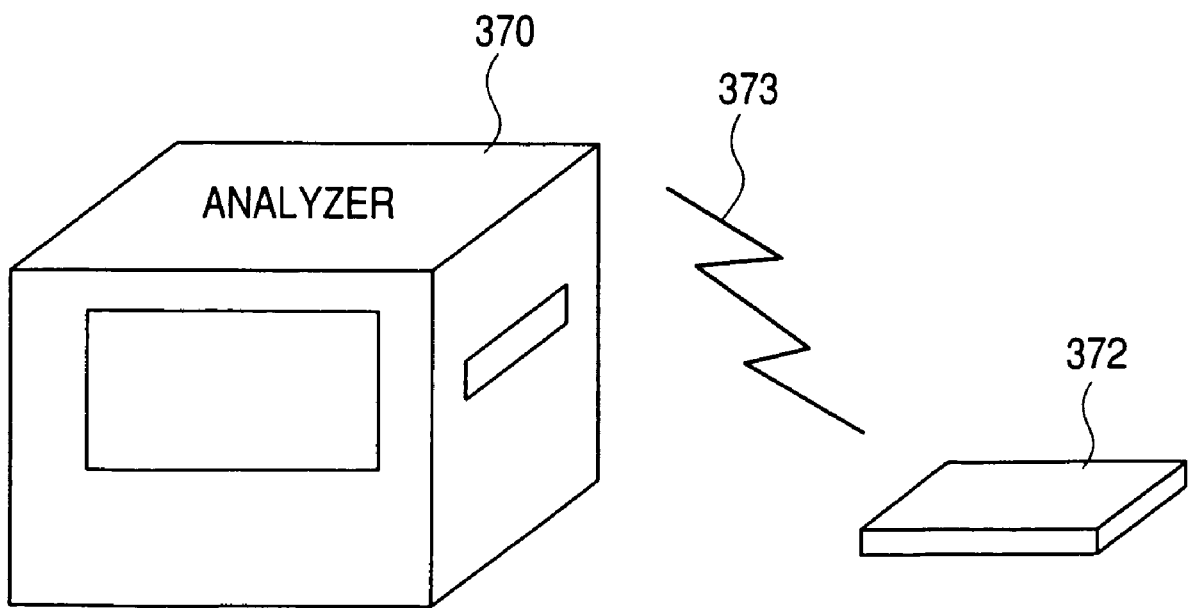

FIGS. 16A and 16B are perspective views simply explaining a method including using the sensing system. In FIG. 16A, a card 372 having the above-mentioned integrated module mounted thereto is inserted into an analyzer 370 through an insertion port 371 to allow a specimen placed on the module or located above the module to be analyzed. Or, there may also be adopted a method in which when a memory is installed in a module device and the module device is inserted into the analyzer 370, previously inspected information is analyzed.

In addition, there may be adopted a method in which as shown in FIG. 16B, the card having the above-mentioned integrated module mounted thereto is provided with a wireless installation, and information is suitably transmitted to an analyzer through wireless communication 373, a method in which a card having the module mounted thereto is connected to a mobile phone or the like to transmit information to an analyzer, or the like.

By adopting such a miniature module using the electromagnetic wave ranging from the millimeter wave to the terahertz wave, it is possible to realize the system which can be readily carried by each individual and with which check of a state of health, check of authentication and security, input of data and positional information to an information apparatus, and the like can be carried out everywhere.

INDUSTRIAL APPLICABILITY

As set forth hereinabove, according to the present invention, it is possible to realize the high frequency electrical signal control device which serves to carry out the sensing using the electromagnetic wave mainly ranging from the millimeter wave to the terahertz wave and which can be readily constructed as the miniature low-power consumption integrated module or the like which is easy in variable control for a state of propagation of the electromagnetic wave through the space, i.e., in control for radiant intensity and beam deflection of the antenna, turn-ON/turn-OFF and the like. As a result, the high frequency electrical signal control device is applied to a living body information inspection system, a baggage security check system, a transmission/reflection imaging system for carrying out material analysis, a radar system for sensing position information in a wireless manner, a pointing device for inputting data to various information apparatuses, and the like to allow the portability of these apparatuses or systems to be enhanced.

The invention claimed is:

1. An electromagnetic wave generating device for generating an electromagnetic wave having a frequency ranging from 30 GHz to 30 THz, including:
    a laser device;
    an optical waveguide for propagating a laser beam emitted from the laser device;
    a photoconductive switch for converting the laser beam propagated through the optical waveguide to the electromagnetic wave; and
    a transmission line comprising a conductor for propagating the electromagnetic wave converted by the photoconductive switch,
    wherein the laser device, the optical waveguide, the photoconductive switch and the transmission line are integrated on a substrate and arranged in a plane of the substrate,
    wherein a first electrode and a second electrode are provided on an upper surface of the photoconductive switch such that a gap is formed between the electrodes at an end of the upper surface, which end is closer to the optical waveguide, and
    wherein the optical waveguide is arranged such that the laser beam propagated through the optical waveguide irradiates a lateral surface of the photoconductive switch, which lateral surface is closer to the optical waveguide, at a portion corresponding to the gap.

2. An electromagnetic wave generating device according to claim 1, wherein an insulator is provided between the substrate and the conductor of the transmission line and the insulator is made of the same material as the optical waveguide.

3. An electromagnetic wave generating device according to claim 1, wherein an insulator is provided between the substrate and the conductor of the transmission line, the insulator and the optical waveguide being made of one and the same material having photosensitivity and being formed in a plane; and wherein the optical waveguide is formed by mask patterning and light exposure techniques such that the optical waveguide has a higher refractive index than the insulator.

4. An electromagnetic wave generating device according to claim 1, wherein the first and second electrodes are connected to the conductor of the transmission line.

5. An electromagnetic wave generating device according to claim 1, wherein the generating device further includes a detection means for detecting the electromagnetic wave propagated through the transmission line as an electrical signal.

6. An electromagnetic wave generating device according to claim 5, wherein the detection means is selected from a Schottky barrier diode, a second photoconductive switch, and a combination of an EO crystal and a photodetector.

7. An electromagnetic wave generating device according to claim 5, wherein the conductor of the transmission line extends from the photoconductive switch to the detection means.

8. An electromagnetic wave generating device according to claim 1, wherein the laser device comprises two laser devices having different oscillation wavelengths and the optical waveguide is a Y-branch optical waveguide, the generating device being capable of operate such that two lights emitted from the two laser devices are mixed with eat other in the Y-branch optical waveguide and introduced into the photoconductive switch and the photoconductive switch generates an electrical signal corresponding to a differential frequency of the two laser devices.

9. An electromagnetic wave generating device according to claim 1, wherein the laser device is capable of emitting a laser pulse, wherein the optical waveguide is capable of propagating the laser pulse emitted from the laser device and dividing the laser pulse into two laser pulses, one of the two laser pulses being converted to the electromagnetic wave in the photoconductive switch while the other being guided to detection means, wherein an optical delay unit for delaying a laser pulse is provided in the optical waveguide extending to the detection means, and wherein a time waveform of a short pulse electrical signal is measured while the optical delay unit varies a delay amount.

10. An electromagnetic wave generating device according to claim 1, wherein the generating device further includes an antenna formed on the substrate, the antenna being capable of radiating an electromagnetic wave propagated through the transmission line to an outer space and receiving an electromagnetic wave from an outer space to propagate it through the transmission line to detection means.

11. A high frequency sensing method comprising,
using the electromagnetic wave generating device according to claim 10, to measure information of an object spaced from the transmission line by detecting the electromagnetic wave propagated through the transmission line as an electric signal using the detection means.

12. A high frequency sensing method comprising,
using the electromagnetic wave generating device according to claim 1, to measure information of an object placed on the transmission line by detecting an electromagnetic wave propagated through the transmission line as an electric signal using a detection means.

* * * * *